United States Patent
Hanes et al.

(10) Patent No.: US 12,102,729 B2
(45) Date of Patent: *Oct. 1, 2024

(54) NATURAL POLYMER-BASED TISSUE ADHESIVE WITH HEALING-PROMOTING PROPERTIES

(71) Applicant: HCS Innovation, LLC, Union Grove, AL (US)

(72) Inventors: Ronnie Michael Hanes, Union Grove, AL (US); Adele Lamping Hanes, Union Grove, AL (US)

(73) Assignee: HCS Innovation, LLC, Union Grove, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/106,684

(22) Filed: Feb. 7, 2023

(65) Prior Publication Data

US 2023/0256135 A1    Aug. 17, 2023

Related U.S. Application Data

(63) Continuation of application No. 17/059,100, filed as application No. PCT/US2019/034530 on May 30, 2019, now Pat. No. 11,571,492, which is a continuation-in-part of application No. 15/994,140, filed on May 31, 2018, now Pat. No. 10,835,635, said application No. 17/059,100 is a continuation-in-part of application No. 16/950,492, filed on Nov. 17, 2020, now abandoned, which is a continuation of application No. 15/994,140, filed on May 31, 2018, now Pat. No. 10,835,635.

(60) Provisional application No. 62/765,437, filed on Aug. 27, 2018, provisional application No. 62/605,185, filed on Aug. 4, 2017.

(51) Int. Cl.
| | |
|---|---|
| *A61L 24/04* | (2006.01) |
| *A61L 24/00* | (2006.01) |
| *A61L 24/08* | (2006.01) |
| *C08L 5/04* | (2006.01) |
| *C08L 5/08* | (2006.01) |
| *C09J 105/00* | (2006.01) |
| *C09J 105/04* | (2006.01) |
| *C09J 105/08* | (2006.01) |

(52) U.S. Cl.
CPC ........... *A61L 24/043* (2013.01); *A61L 24/001* (2013.01); *A61L 24/0026* (2013.01); *A61L 24/08* (2013.01); *C09J 105/00* (2013.01); *C09J 105/04* (2013.01); *C09J 105/08* (2013.01); *A61L 2400/04* (2013.01); *C08L 5/04* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 5,428,014 A | 6/1995 | Labroo et al. | |
| 5,836,970 A * | 11/1998 | Pandit | A61L 15/225 606/151 |
| 6,341,608 B1 | 1/2002 | Akervall | |
| 8,795,713 B2 | 8/2014 | Makower et al. | |
| 8,829,075 B2 | 9/2014 | Bianco-Peled et al. | |
| 9,381,270 B2 | 7/2016 | Makower et al. | |
| 2007/0167971 A1 | 7/2007 | Huey et al. | |
| 2008/0215090 A1 | 9/2008 | Gonzales et al. | |
| 2009/0291912 A1 | 11/2009 | Tijsma et al. | |
| 2010/0152730 A1 | 6/2010 | Makower et al. | |
| 2011/0015759 A1* | 1/2011 | Bianco-Peled | A61P 17/02 623/23.72 |
| 2012/0108509 A1 | 5/2012 | Hissong et al. | |
| 2013/0018320 A1 | 1/2013 | McKay | |
| 2013/0039899 A1* | 2/2013 | Preiss-Bloom | A61B 17/00491 424/94.5 |
| 2014/0296293 A1 | 10/2014 | Andersen et al. | |
| 2015/0045507 A1 | 2/2015 | Bender et al. | |
| 2016/0008513 A1 | 1/2016 | Cherry et al. | |
| 2016/0151532 A1 | 6/2016 | Rubin et al. | |
| 2017/0281781 A1* | 10/2017 | Park | A61K 9/0019 |
| 2017/0326171 A1 | 11/2017 | Diehn et al. | |

FOREIGN PATENT DOCUMENTS

| | | |
|---|---|---|
| CN | 105617451 | 6/2016 |
| WO | WO 2013/078550 | 6/2013 |
| WO | WO 2014/172703 | 10/2014 |
| WO | WO 2016/176186 | 11/2016 |

OTHER PUBLICATIONS

Baumann et al., Carbohydrate Polymers as Adhesives, Handbook of adhesive technology, 1994, Ch 15, pp. 299-313.
El-Kamel et al., Chitosan and Sodium Alginate-Based Bioadhesive Vaginal Tablets, AAPS PharmSci, vol. 4, No. 4, Article 44, 2002, pp. 1-7.
Feldman, Adhesion and Hemostasis in Surgery, Encyclopedia of Materials: Science and Technology, 2001, pp. 38-43.
Honary et al., The effect of chitosan molecular weight on the properties of alginate/chitosan microparticles containing prednisolone, Tropical Journal of Pharmaceutical Research, vol. 8, No. 1, 2009, pp. 53-61.

(Continued)

*Primary Examiner* — Kyung S Chang
(74) *Attorney, Agent, or Firm* — Pandiscio & Pandiscio

(57) ABSTRACT

A tissue adhesive for contacting a tissue site, the tissue adhesive comprising: a mixture of natural polymers; and an activating agent enhancing the adhesive properties of the mixture of natural polymers. And a tissue adhesive for contacting a tissue site, the tissue adhesive comprising: a mixture of natural polymers; and an aqueous solution of a water soluble starch or a water soluble starch derivative which forms a gel with the addition of the mixture of natural polymers.

21 Claims, No Drawings

(56) References Cited

OTHER PUBLICATIONS

Kucharska et al., Dressing Sponges Made of Chitosan and Chitosan-Alginate Fibrids, Fibres & Textiles in Eastern Europe, vol. 16, No. 3, 2008, pp. 109-113.

Li, et al., Chitosan-alginate hybrid scaffolds for bone tissue engineering, Biomaterials, Jun. 2005, vol. 26, No. 18, pp. 3919-3928.

Murakami et al., Hydrogel Blends of Chitin/Chitosan, Fucoidan and Alginate as Healing-Impaired Wound Dressings, Biomaterials, vol. 31, No. 1, 2010, pp. 83-90.

Patel et al., Chitosan: Emergence as Potent Candidate for Green Adhesive Market, Biochemical Engineering Journal, 2015, vol. 102, pp. 74-81.

Patel et al., Development of a Chitosan-Based Adhesive: Application to Wood Bonding, J. Appl. Polym. Sci., 2013, vol. 127, pp. 5014-5021.

Patel et al., Preparation of Chitosan-Based Adhesives and Assessment of their Mechanical Properties, Appl. Polym. Sci., 2013, vol. 127, pp. 3869-3876.

Vakalopoulos et al., Mechanical Strength and Rheological Properties of Tissue Adhesives With Regard to Colorectal Anastomosis: An Ex Vivo Study, Annals of Surgery, vol. 261, No. 2, 2015, pp. 323-331.

Wang et al., Feasibility of Chitosan-alginate (Chi-Alg) hydrogel used as scaffold for neural tissue engineering: a pilot study in vitro, Biotechnology & Biotechnological Equipment, 2017, pp. 1-9.

Wu et al., A soft tissue adhesive based on aldehyde-sodium alginate and amino-carboxymethyl chitosan preparation through the Schiff reaction, Frontiers of Material Science, vol. 11, No. 3, 2017, pp. 215-222.

\* cited by examiner

NATURAL POLYMER-BASED TISSUE ADHESIVE WITH HEALING-PROMOTING PROPERTIES

REFERENCE TO PENDING PRIOR PATENT APPLICATIONS

This patent application is a continuation of prior U.S. patent application Ser. No. 17/059,100, filed Nov. 25, 2020 by HCS Innovation, LLC for NATURAL POLYMER-BASED TISSUE ADHESIVE WITH HEALING-PROMOTING PROPERTIES, which patent application:

(A) is a 371 national stage entry of prior International (PCT) Patent Application No. PCT/US19/34530, filed May 30, 2019 by HCS Innovation LLC for NATURAL POLYMER-BASED TISSUE ADHESIVE WITH HEALING-PROMOTING PROPERTIES, which patent application in turn:
  (i) is a continuation-in-part of prior U.S. patent application Ser. No. 15/994,140, filed May 31, 2018 by HCS Innovation, LLC for NATURAL POLYMER BASED TISSUE ADHESIVE WITH HEALING PROMOTING PROPERTIES; and
  (ii) claims benefit of prior U.S. Provisional Patent Application Ser. No. 62/765,437, filed Aug. 27, 2018 by Ronnie Michael Hanes et al. for TISSUE ADHESIVE WITH HEALING PROMOTING PROPERTIES INCORPORATING NATURAL POLYMERS; and (B) is a continuation-in-part of prior U.S. patent application Ser. No. 16/950,492, filed Nov. 17, 2020 by HCS Innovation, LLC for NATURAL POLYMER BASED TISSUE ADHESIVE WITH HEALING PROMOTING PROPERTIES, which patent application is a continuation of prior U.S. patent application Ser. No. 15/994,140, filed May 31, 2018 by HCS Innovation, LLC for NATURAL POLYMER BASED TISSUE ADHESIVE WITH HEALING PROMOTING PROPERTIES, which patent application in turn claims benefit of prior U.S. Provisional Patent Application Ser. No. 62/605,185, filed Aug. 4, 2017 by Ronnie Michael Hanes et al. for POST-MUCOSAL TISSUE SURGERY HEALING DEVICE.

The six (6) above-identified patent applications are hereby incorporated herein by reference.

FIELD OF THE INVENTION

The invention relates to the field of medical adhesives and sealants. More specifically, the invention relates to a tissue adhesive formed from a mixture of natural polymers in combination with an activating agent that enhances the adhesive properties of the natural polymer mixture.

In addition, a method of forming a tissue adhesive comprising a stable gel of the natural polymers with the addition of a water soluble starch or starch derivative is disclosed.

Specific applications of various forms of the tissue adhesive are also disclosed.

BACKGROUND OF THE INVENTION

Tissue adhesives for use in the body have very demanding criteria for use, and many adhesives used elsewhere, such as cyano-acrylates, cannot be used internally due to toxicity. Also, it is desirable that tissue adhesives for internal use be not only bio-compatible but also absorbable such that there is no need for removal as tissue re-growth proceeds. This creates a challenge for the development of a tissue adhesive for internal use. Skin irritation is also a factor in formulating materials for application to burn or skin donor sites. More benign tissue adhesives have other complications. For example, fibrin-based adhesives have poor mechanical strength and pose a risk of viral infection. Current starch-based adhesives require a cross-linking agent which might not be bio-compatible or might cause irritation. Thus a tissue adhesive with mechanical strength and good adhesion that is formulated using only bio-compatible and bio-absorbable materials would be advantageous. Formulating the tissue adhesive using only naturally-derived materials is desirable as well.

Several tissue adhesives based on natural polymers have been developed but these formulations typically use a cross-linking agent with aldehyde or amine functional groups along with the natural polymers or modified versions of the natural polymers. For example, A. El-Kamel et al., "*Chitosan and Sodium Alginate-Based Bioadhesive Vaginal Tablets*", AAPS PharmSci 2002: 4(4), article 44, developed formulations for bio-adhesive tablets as a means for vaginal introduction of metronidazole. In this case, the formulations included 20% of the drug metronidazole, chitosan and sodium alginate along with microcrystalline cellulose and/or sodium carboxymethylcellulose. Chitosan rods were formed from a paste with acetic acid and dried. These were then cross-linked with glutaraldehyde and compounded with the other ingredients and pressed into tablets. The adhesion of the tablets to rabbit intestinal mucosa was measured and, for most formulations, was observed to be 20 grams/sq. centimeter, with one formulation exhibiting 30 grams/sq. centimeter adhesion. The tablets were observed to completely dissolve in distilled water or a pH 4.8 buffer in about 6 hours. Not only is the formulation complicated and uses an aldehyde cross-linking agent, but the short lifetime of the adhesive on exposure to liquids renders it not useful for tissue adhesive applications other than drug release.

Y. Wu et al., "*A soft tissue adhesive based on aldehyde-sodium alginate and amino-carboxymethyl chitosan preparation through the Schiff reaction*", Frontiers of Material Science, 2017, 11(3): 215-222, DOI 10:1007/s11706-017-0392-x, explored a soft tissue adhesive formulation. The authors oxidized the alcohol function of sodium alginate to form aldehyde groups. Carboxymethyl chitosan was modified to produce amino-carboxymethyl chitosan. Mixing various ratios of aqueous solutions of these materials formed a hydrogel in about 10 minutes. The resulting adhesives provided shear adhesion with porcine skin up to 20-30 grams/sq. centimeter. However, this was obtained after pressing the porcine skin sections with a 50 gram loading for 10 minutes. Not only are "functionalized natural" (rather than "totally natural") polymers used in the formulation, the 10 minute press time required to provide the reported adhesion is impractical for a surgical procedure in which the tissue adhesive is used. There was no mention of an adhesive activator or evaluation of durability on exposure to body fluids.

U.S. Patent Publication No. 2017/0326171 describes a hemostatic putty with tissue adhesive properties which includes polysaccharides in the formulation. In contrast to the present invention, this patent publication lists the polysaccharide as only one possible part of a four part composition that includes, in addition to the biopolymer of which chitosan or alginates are possibilities, a secondary polymer (with polyvinyl alcohol cited as the only example), an ionic cross-linker (such as a borate) and a solvent (either water or an organic solvent). There is no combination of natural polymers cited, as well as no mention of an activator to enhance adhesion. In addition, although adhesion is mentioned, there is no data presented for adhesion measurements or for durability on exposure to bodily fluids.

U.S. Pat. No. 6,341,608 describes the use of a tissue adhesive to coat a tumor before removal. Although alginates are listed as possible adhesive materials, there is no citation of a second natural polymer in combination with the alginates. Also, no activator to enhance adhesion is listed, and no adhesion data is presented for the tissue adhesive.

Particular applications for a tissue adhesive for which no approved material is currently available include tonsillectomy and adenoidectomy surgeries. These are common procedures that often lead to bleeding and pain. Post-operative pain is exacerbated by swallowing, and solid food is generally avoided for the first few days. Improved surgical procedures have been developed that reduce trauma to the delicate mucosal tissue, but pain and bleeding continue to be associated with these procedures for many days post-surgery. An adhesive material to form a barrier over the surgery site is desirable, but this application is very demanding. The material must provide adhesion to the surgical site (muscle tissue which has been electrically cauterized), be flexible enough to allow flexing of the jaw and yet be mechanically firm enough to show durability in the environment during swallowing. The material used must be easily and simply applied to the surgery site with minimal manipulation and pressure to achieve adhesion. Also, the material must endure the moist environment and exposure to liquids, both saliva and ingested liquids, without loss of integrity for a period of at least two days post-surgery.

The situation is further complicated by the nature of the delicate mucosal tissue. This tissue is, by nature, wet and this wet state must be maintained for healing. The wet state prevents the use of classic bandage material due to lack of adhesion to the wet tissue. Furthermore, a classic bandage is a potential choking hazard due to lodging in the throat if it detaches. Obviously, this is an especially serious problem for children, the most common group to experience these tonsillectomy and adenoidectomy surgeries.

Pain and swelling of the traumatized tissue is also an issue, and direct topical application of a pain reliever could be desirable. However, direct administration of a pain reliever is difficult as well as problematic. Topical administration is also inconsistent other than during an in-patient stay. Typical topical administration of a pain reliever in the throat would be short-lived due to "washing away" or erosion of the pain reliever.

In addition, a means to accelerate healing of the wound site would be beneficial by shortening the recovery time after surgery. Any means to accomplish this must take into consideration maintaining the "wet" state of the oral tissue and avoiding any choking hazard from detachment of any device placed in the throat.

A post-tonsillectomy device developed for these purposes would also be useful for other procedures in the ear, nose and throat area. A tissue adhesive developed for this purpose also has potential use in other areas such as burn sites or skin graft donor sites.

Thus there exists a need for a new type of bandage or dressing material for use as a device that would be suitable for use post tonsillectomy surgery. Ideally, this "device" (i.e., the bandage or dressing material) would combine a number of functions to alleviate pain, bleeding and trauma. These include an adhesive component such that a typical bandage adhesive (which could cause irritation and further trauma to the wound area) is not necessary. There should be a component that accelerates healing of the wound site in order to shorten recovery time. Optionally, there could be a hemostatic component to control bleeding at the wound site, and/or a therapeutic component that alleviates pain and swelling from the surgery trauma. Obviously it would be most beneficial if all components are hypoallergenic as well as bio-compatible. In order to prevent choking hazards if the device loses adhesion and comes free, it would also be beneficial if the "device" (i.e., the bandage or dressing material) was in the form of a soft material or readily broke into small pieces rather than coming free as a large single entity.

Despite the obvious need, prior attempts have not been successful in fully addressing or solving the need, since only one or two aspects of the stated needs (at most) are accomplished by prior art devices. Significantly, the inventors have discovered a means to meet all of these needs and develop the novel solution to the problem described herein.

In addition to the foregoing, skin wound healing devices typically rely on one type of healing mechanism, such as an anti-microbial healing mechanism, "wet" healing solutions such as colloidal bandages, or increased localized oxygen such as oxygen-generating compounds or hyperbaric healing. A particular application for the present invention would be for a skin graft donor or burn site where localized pain is experienced by the patient. The combination of accelerated healing from the materials used, as well as the soothing action from the "wet" environment of the gel used in one optional form of the invention, would reduce the pain as well as decreasing the healing time. Also, analgesics could be added to the gel to further reduce the pain.

ADDITIONAL RELATED PRIOR ART

One example of additional related prior art is U.S. Patent Publication No. 2012/0108509, which describes a means to create an artificial scab for use in airways, comprising applying a dry powder composed of chitosan and a partially-oxidized polysaccharide such as cellulose or starch. The dry powder is used to adhere to body tissues but no adhesion strength data are reported. There is also no mention of an activating agent to increase adhesion.

U.S. Patent Publication No. 2016/0151532 describes a hemostatic patch and includes a description of the use of chitosan, but not in combination with an alginate. The claims read to a muco-adhesive and a vasoconstrictant such as neuropeptide Y, epinephrine, etc., and the publication does not report adhesion data or cite an adhesion activator for the powder. No evaluation of durability for internal use is mentioned.

U.S. Pat. No. 8,795,713 describes a mucosal tissue dressing based on methyl cellulose. The aim of this invention is to provide a method to reduce abrasion of a tonsil removal site as seen in claim 1 of the patent. Other than reducing site trauma by avoiding abrasion from solid particles in the throat, the device does not anticipate or provide any of the desirable functions set forth in the foregoing problem statement of the present invention. The specification section of the '713 patent mentions the use of chitosan, chitin and alginates as part of a long list of potential base polymers for the bandage, but not in combination, and also does not provide any enabling examples of their use. In addition, no adhesion data is reported and there is no citation of an activator to enhance adhesion. No mention of durability was found in the patent.

R. D. Rogers, G. Gurau, J. Shamshina and D. T. Daly in International (PCT) Patent Publication No. WO 2014172703 describe a combination of fibers of chitin and alginic acid that accelerate wound healing, as well as methods to produce and use the fibers. Therapeutics such as Vitamin E can be incorporated into the fibers. The composite fibers were incorporated into a typical external wound bandage and shown to be effective in accelerating wound healing versus either a standard bandage or competitive products currently on the market. The bandage material used incorporated a typical, prior art adhesive material for attachment to the skin.

Magdalena Kucharska, Antoni Niekraszewicz, Maria Wisniewska-Wrona, Kinga Brzoza-Malczewska, "*Dressing Sponges Made of Chitosan and Chitosan-Alginate Fibrids*", FIBRES & TEXTILES in Eastern Europe, July/September 2008, Vol. 16, No. 3 (68), present a manufacturing process for biological chitosan and chitosan-alginate dressing sponges as well as their biological and physical-mechanical properties. The sponge of chitosan-alginate microfibrids, with an addition of calcium in the in vitro contact with citrate plasma, activates the plasma clotting system to a higher degree, resulting in the shortening of the clotting time of both of the endogenous and exogenous systems when compared with the sponge made of chitosan microfibrids. There is no mention of promotion of activation of the material for improved adhesion, nor is there any data reporting adhesion.

K. Murakami, H. Aoki, S. Nakamura, S. Nakamura, M. Takikawa, M. Hanzawa, S. Kishimoto, H. Hattori, Y. Tanaka, T. Kiyosawa, Y. Sato and M. Ishihara, "*Hydrogel blends of chitin/chitosan, fucoidan and alginate as healing-impaired wound dressings*", Biomaterials 31 (2010) 83-90, describe preparation of a hydrogel sheet composed of a blended powder of alginate, chitin/chitosan, fucoidan and ethylene glycol diglycidyl ether (cross-linking agent) for evaluation as a wound healing material. The material was more effective at promoting wound healing than no added material or alginate alone. There is no mention of the addition of therapeutic agents or of adhesion data. There is also no use of an adhesion activator. Hydrogel sheets were placed on external wound sites and held in place by wrapping with plastic sheets, and thus are not amenable for use on a tonsillectomy site. The hydrogel is also different in nature to the gel described in the present invention, as well as not meeting all of the desired criteria listed above in the aforementioned problem statement of the present invention. Also missing from this article is any description of a means to increase the durability of the material or durability measurements.

S. Honary, M. Maleki and M. Karami, "*The Effect of Chitosan Molecular Weight on the Properties of Alginate/Chitosan Microparticles Containing Prednisolone*", Tropical Journal of Pharmaceutical Research, February 2009, 8(1); 53-61, describe combinations of solutions of chitosan with alginate and calcium chloride solutions to create microparticles for use as drug delivery and release agents. Although a combination of natural polymers is described, this was not for use as a tissue adhesive and the polymers were in solution when combined, not in powder form. No adhesion activating agent was used in this work. Also, adhesion was measured as the number of particles adhering to a section of rat small intestine, in line with the stated use for drug delivery and not as a tissue adhesive. No mention of durability for internal use or increased adhesion by use of an activator was found in the publication.

SUMMARY OF THE INVENTION

Thus it can be seen that there exists an unmet need for a tissue adhesive that would be suitable for use post tonsillectomy surgery or other mucosal tissue surgery, as well as many other applications. This tissue adhesive can be used as a "device" (i.e., the applied tissue adhesive) that includes adhesive properties and wound healing-accelerating properties, as well as being used as a surface layer protective from abrasion at the surgery site. Significantly, the novel tissue adhesive is biocompatible and biodegradable, such that it can be left at a tissue site and will naturally break down over time. The inventors, surprisingly, discovered that a novel powder as formulated from a mixture of natural polymers provided increased adhesive strength when an activating agent was added to the mixture. In one form of the invention, the mixture of natural polymers is composed of polysaccharides (e.g., chitosan and an alginate such as sodium alginate). The mixture of natural polymers can be in powder form. The activating agent employed is a dilute acid solution, preferably a carboxylic acid such as acetic acid, lactic acid or similar acid.

The activating agent can be mixed with the natural polymer powder to form a gel or other composition. Where it is desired to form a gel, the proportions of the activating agent and the natural polymer powder is adjusted as needed to form a gel of the desired consistency. In one form of the invention, the gel may be delivered by syringe or a manual applicator. Or the activating agent can be sprayed onto the tissue site and the dry natural polymer powder added to the site, with an optional second spray of the activating agent over the natural polymer powder.

The activating agent can also be sprayed onto the surgery site and the natural polymer mixture may be applied as a thin film device using a binding agent that may be dissolved by body fluids. In other words, in this form of the invention, the natural polymer mixture may be formed into a thin film device using a binding agent which is dissolved by body fluids, the activating agent can be sprayed onto the surgery site, and the natural polymer mixture thin film device can be placed on top of the activating agent. Additional activating agent may thereafter be sprayed onto the natural polymer mixture thin film device.

The inventors also, unexpectedly, found a synergistic effect for increased adhesion with the activation agent by a combination of chitosan and sodium alginate powders, in that the combination of the chitosan and sodium alginate powders provided greater adhesion than either the chitosan powder or the sodium alginate powder when used alone.

It was also discovered that the durability and toughness of the gel formed can be increased by treating the surface of the gel with a solution of a salt containing a divalent cation. Examples of these salts include calcium chloride, calcium acetate or calcium carbonate.

A further embodiment of the present invention is to form a thin film of the gel material for ease of application to the desired site. This thin film of the gel material may be formed by drying the gel material. By drying the gel material to a greater extent, this drying may result in a "dry" thin film; or by drying the gel material to a lesser extent, this drying may result in a "wet" thin film.

The combination of a mixture of chitosan and sodium alginate powders, along with an activation agent in the form of a dilute acid solution, provides accelerated wound healing and a high degree of adhesion to the tissue at the surgical site.

The combination of chitosan and alginates is well known to promote or accelerate wound healing, with many examples in the literature.

The addition of an activation agent in the form of a dilute acid solution renders the combination of chitosan and alginate significantly more adhesive, thereby making it practical to use as a cover for a surgical site.

In addition, a toughening treatment of the surface of a gel with the foregoing composition with a dilute solution of a calcium salt provides increased durability and resistance to bodily fluids, whereby to provide abrasion resistance with the underlying gel providing adhesion and healing properties.

In another form of the present invention, the natural polymer powder, or the natural polymer powder with activating agent, is added to an aqueous solution of a water soluble starch or a water soluble starch derivative in order to form a stable gel that is simple to work with, e.g., for application by a syringe or a manual applicator, and enhances the healing properties of the natural polymer powder without decreasing the adhesive properties. Note that in this form of the invention, the use of the activating agent is optional, depending on the functionality required for a particular application. For example, the activating agent might not be needed for use of the gel on a skin graft donor site, where only modest adhesion may be necessary. Regardless of whether the activating agent is used, in this form of the invention, after the gel has been applied, the surface of this gel can also be toughened with a dilute solution of a calcium salt if desired.

A further embodiment of the invention is to form a thin film of the gel material for ease of application to the desired site. This thin film of the gel material may be formed by drying the gel material. By drying the gel material to a greater extent, this drying may result in a "dry" thin film; or by drying the gel material to a lesser extent, this drying may result in a "wet" thin film.

In one preferred form of the invention, there is provided a tissue adhesive for contacting a tissue site, the tissue adhesive comprising:
 a mixture of natural polymers; and
 an activating agent enhancing the adhesive properties of the mixture of natural polymers.

In another preferred form of the invention, there is provided a method comprising:
 positioning a tissue adhesive on a tissue site, wherein the tissue adhesive comprises:
  a mixture of natural polymers; and
  an activating agent enhancing the adhesive properties of the mixture of natural polymers.

In another preferred form of the invention, there is provided a tissue adhesive for contacting a tissue site, the tissue adhesive comprising:
 a mixture of natural polymers; and
 an aqueous solution of a water soluble starch or a water soluble starch derivative which forms a gel with the addition of the mixture of natural polymers.

In another preferred form of the invention, there is provided a method comprising:
 positioning a tissue adhesive on a tissue site, wherein the tissue adhesive comprises:
  a mixture of natural polymers; and
  an aqueous solution of a water soluble starch or a water soluble starch derivative which forms a gel with the addition of the mixture of natural polymers.

DETAILED DESCRIPTION OF THE PREFERRED EMBODIMENTS

Definitions

For the purposes of the present invention, the term "natural polymer" is intended to mean a polymer of plant or animal origin. An alternative term for this is a "bio-polymer".

For the purposes of the present invention, the term "polysaccharides" is intended to mean polymeric carbohydrate molecules composed of long chains of monosaccharide units bound together by glycosidic linkages, which on complete hydrolysis give the constituent monosaccharides or oligosaccharides. Examples include storage polysaccharides such as starch and glycogen, and structural polysaccharides such as cellulose and chitin.

For the purposes of the present invention, the term "a partial hydrolysis derivative of a polysaccharide" is intended to mean a derivative in which all or a portion of the side chain functional groups are hydrolysed but there is not complete hydrolysis of the polymeric chain to form monomers. An example of a partial hydrolysis derivative of a polysaccharide is chitosan as a product of partial hydrolysis of the acetyl amine function of chitin.

For the purposes of the present invention, the term "a water soluble starch derivative" is intended to mean a starch which has been treated in any manner to produce a derivative with increased water solubility. An example of a water soluble starch derivative is pullulan, a polysaccharide polymer consisting of maltotriose units. Pullulan is produced by fermentation of starch by the fungus *Aureobasidium pullulans*.

For the purposes of the present invention, the term "a neutralization salt of a polysaccharide" is intended to mean the product of the reaction between a base and the carboxylic acid function of the polysaccharide. An example of a neutralization salt of a polysaccharide is the reaction of sodium hydroxide with alginic acid to yield sodium alginate.

For the purposes of the present invention, the term "an alginate" is intended to mean alginic acid or an ester of alginic acid or a salt of alginic acid.

For the purposes of the present invention, the term "a dilute solution of an acid" is intended to mean an aqueous solution containing less than 20% by weight of the designated acid. Similarly, a dilute solution of a salt contains less than 20% by weight of the salt.

For the purposes of the present invention, the term "a toughening treatment of an adhesive gel" is intended to mean a chemical cross-linking that allows the gel to retain firmness and/or integrity or reduce fluid absorption when exposed to bodily fluids.

For the purposes of the present invention, the term "a workable gel" is intended to mean a gel which is easily manipulated for placement at the desired site.

Composition Comprising Mixture of Natural Polymers with Activating Agent

The "device" of the present invention is a combination of materials which meet the criteria as outlined above. The materials suitable for this device include mixtures of natural polymer compounds (which provide wound healing properties) combined with an activating agent (which provides increased adhesive strength). Significantly, the novel tissue adhesive is biocompatible and biodegradable, such that it can be left at a tissue site and will naturally break down over time.

The mixtures of natural polymer compounds may comprise polysaccharides or partial hydrolysis derivatives of polysaccharides or neutralization salts of polysaccharides. Preferred natural polymer compounds include chitosan or chitin powder combined with an alginate such as alginic acid or salts of this acid (e.g., sodium alginate). These compounds have recognized therapeutic healing benefits. The mixture of natural polymer compounds can be in powder form. In one preferred form of the invention, the mixture of natural polymers comprises chitosan and sodium alginate, wherein the ratio of sodium alginate to chitosan is between 10:90 and 90:10. In another preferred form of the invention, the mixture of natural polymers comprises chitosan and sodium alginate, wherein the ratio of sodium alginate to chitosan is between 25:75 and 75:25.

The adhesion of the mixture of natural polymer compounds is enhanced through use of an activating agent such as a dilute aqueous solution of an acid. In one preferred form of the invention, the activating agent comprises a carboxylic acid solution (e.g., acetic acid, lactic acid, etc.).

The activating agent can be mixed with the natural polymer powder to form a gel or other composition. Where it is desired to form a gel, the proportions of the activating agent and the natural polymer powder is adjusted as needed to form a gel of the desired consistency. In one form of the invention, the gel may be delivered by syringe or a manual applicator. Or the activating agent can be sprayed onto the tissue site and the dry natural polymer powder added to the site, with an optional second spray of the activating agent over the natural polymer powder.

The activating agent can also be sprayed onto the surgery site and the natural polymer mixture may be applied as a thin film device using a binding agent that may be dissolved by body fluids. In other words, in this form of the invention, the natural polymer mixture may be formed into a thin film device using a binding agent which is dissolved by body fluids, the activating agent can be sprayed onto the surgery site, and the natural polymer mixture thin film device can be placed on top of the activating agent. Additional activating agent may thereafter be sprayed onto the natural polymer mixture thin film device.

The inventors also, unexpectedly, found a synergistic effect for increased adhesion with the activation agent by a combination of chitosan and sodium alginate powders, in that the combination of the chitosan and sodium alginate powders provided greater adhesion than either the chitosan powder or the sodium alginate powder when used alone.

It was also discovered that the durability and toughness of the gel formed can be increased by treating the surface of the gel with a solution of a salt containing a divalent cation. Examples of these salts include calcium chloride, calcium acetate or calcium carbonate.

A further embodiment of the present invention is to form a thin film of the gel material for ease of application to the desired site. This thin film of the gel material may be formed by drying the gel material. By drying the gel material to a greater extent, this drying may result in a "dry" thin film; or by drying the gel material to a lesser extent, this drying may result in a "wet" thin film.

The combination of a mixture of chitosan and sodium alginate powders, along with an activation agent in the form of a dilute acid solution, provides accelerated wound healing and a high degree of adhesion to the tissue at the surgical site.

The combination of chitosan and alginates is well known to promote or accelerate wound healing, with many examples in the literature.

The addition of an activation agent in the form of a dilute acid solution renders the combination of chitosan and alginate significantly more adhesive, thereby making it practical to use as a cover for a surgical site.

In addition, a toughening treatment of the surface of a gel with the foregoing composition with a dilute solution of a calcium salt provides increased durability and resistance to bodily fluids, whereby to provide abrasion resistance with the underlying gel providing adhesion and healing properties.

Depending on the need, therapeutic agents can be added to the "device" (i.e., the mixture of natural polymers combined with the activating agent), e.g., vitamins, analgesics (such as acetaminophen or an NSAID), vasoconstricters (such as neuropeptide Y, epinephrine) or anesthetics (examples include, but are not limited to: lidocaine, benzocaine, bupivacaine, levobupivacaine, ropivacaine, etidocaine or articaine), in any appropriate combination. Also an anti-infective (such as Primaxin or Pentamycetin) may be incorporated into the device as a means of immediate action to prevent infection, with the chitin/chitosan providing longer term infection control.

In another form of the invention, the tissue adhesive "device" is formed by adding the mixture of natural polymer powders to an aqueous solution of a water soluble starch or a water soluble starch derivative in order to form a stable gel that is simple to work with, e.g., for application by a syringe or a manual applicator, and enhances the healing properties of the natural polymer powder without decreasing the adhesive properties. Significantly, the novel tissue adhesive is biocompatible and biodegradable, such that it can be left at a tissue site and will naturally break down over time. Note that in this form of the invention, the use of the activating agent is optional, depending on the functionality required for a particular application. For example, the activating agent might not be needed for use of the gel on a skin graft donor site, where only modest adhesion may be necessary. Or, where substantial adhesion is required, the combination of a mixture of natural polymer powders with an activating agent is added to an aqueous solution of a water soluble starch or a water soluble starch derivative in order to form a stable gel which has substantial therapeutic healing properties with substantial adhesive properties.

Regardless of whether the activating agent is used, in this form of the invention, after the gel has been applied, the surface of this gel can also be toughened with a dilute solution of a calcium salt if desired.

Thus in this form of the invention, the combination of a mixture of natural polymer compounds is added to a solution of a water soluble starch or a water soluble starch derivative to form a stable gel (the "device"). This gel has therapeutic healing properties. If increased adhesion is required, the combination can also include the activating agent.

A further embodiment of the invention is to form a thin film of the gel material for ease of application to the desired site. This thin film of the gel material may be formed by drying the gel material. By drying the gel material to a greater extent, this drying may result in a "dry" thin film; or by drying the gel material to a lesser extent, this drying may result in a "wet" thin film.

Depending on the need, therapeutic agents can be added to the device, e.g., vitamins, analgesics (such as acetaminophen or an NSAID), vasoconstricters (such as neuropeptide Y, epinephrine) or anesthetics (examples include, but are not limited to: lidocaine, benzocaine, bupivacaine, levobupivacaine, ropivacaine, etidocaine or articaine), in any appropriate combination. Also an anti-infective (such as Primaxin or Pentamycetin) may be incorporated into the device as a means of immediate action to prevent infection, with the chitin/chitosan providing longer term infection control.

Exemplary Uses

A tissue adhesive as described above (the "device") could be placed inside a cavity which is then closed with the tissue adhesive, used to create an external dressing for a surgery site by application as a gel, thin film device or dry powder, or any methods in combination. The tissue adhesive could also be applied to an external wound site, with or without an additional protective material.

For example, as part of a tonsillectomy surgery, a pouch or flap could be formed at the surgery site and a device formed in accordance with the present invention may be placed inside the pouch or flap before the site is closed. The device could be in the form of a gel, lozenge or similar form that is of suitable size, or enclosed in a thin film, envelope or capsule formed of a material that is quickly dissolved by the body for rapid release of the active ingredients.

Another option, either in combination with the implanted device described above (i.e., the tissue adhesive) or separately, is to apply the adhesive mixture as a dry powder externally to the surgery site after the site is closed. This would provide control of bleeding, increased rate of wound healing as well as alleviation of pain and swelling. In this case, no additional materials for adhesion, other than the adhesion activator described above, may be required due to the adhesive properties of the sodium alginate:chitosan powder in combination with the adhesion activator. The nature of the powder applied in this manner, rather than as a classic bandage, avoids creating a choking hazard as the material is released in small, friable pieces that could be either swallowed with no harm or ejected orally. The lack of a separate adhesive compound reduces the possibility of irritation of mucosal tissue.

Another option is to incorporate the adhesive powder into a thin film device with a binding agent that is dissolved by body fluids. The thin film device could then be placed onto the surgery site (optionally after the site is wet with an activating compound) to provide a thin layer of the adhesive powder with the desired properties as described above. Optionally, once in place, the thin film could be sprayed with the activating compound and/or subjected to a toughening treatment with a compound having a divalent cation to increase resistance of the film to bodily fluids while maintaining adhesion.

Yet another option is to incorporate the adhesive powder into a gel by mixing the adhesive powder with a water soluble starch or a water soluble starch derivative to form a more stable tissue adhesive gel with "wet" healing properties. An aqueous solution of the activating compound may, optionally, be added to the gel or the activating compound could be applied to the surgery site separately. This gel would then be placed onto the surgery site for adhesion to form a protective device. Optionally, once in place, the gel could be subjected to a toughening treatment with a compound having a divalent cation to increase resistance of the gel to bodily fluids while maintaining adhesion.

Alternatively, the gel as described above (i.e., the mixture of natural polymers combined with a water soluble starch or a water soluble starch derivative) could be applied externally to a skin donor or graft site or to a burn site (for example) for protection and to promote healing. In this case, the optional activating agent for enhancing adhesion may not be necessary, and the optional toughening treatment may not be necessary if the gel is covered by a conventional protective material.

Thus it is seen that the desired properties and functions of a protective device that also promotes healing for post-surgery use may be achieved through a novel combination of compounds and thus provide a viable solution to a problem for which no practical solution has previously existed.

With no additional adhesives needed and the healing properties of the combined powders, the formulations detailed herein could find uses in other applications such as burn sites and skin donor sites.

In one particularly preferred application, a tissue adhesive, comprising a mixture of natural polymers and an activating agent enhancing the adhesive properties of the mixture of natural polymers, is positioned on a surgical site created during tonsillectomy surgery, or a surgical site created during an adenoidal surgery, or a surgical site created during another surgical procedure, with the tissue adhesive adhering to the surgical site and acting as a healing promoter and as a protective cover for the surgical site until the tissue adhesive subsequently breaks down. In this form of the invention, the tissue adhesive may be engineered to break down several (e.g., 2-4) days after surgery. In this form of the invention, the tissue adhesive may be in the form of a gel or a thin film device.

In another particularly preferred application, a tissue adhesive, comprising a mixture of natural polymers and an activating agent enhancing the adhesive properties of the mixture of natural polymers, is positioned at a joinder site between two pieces of tissue, with the tissue adhesive acting as an adhesive to join the two pieces of tissue until tissue regrowth and the tissue adhesive subsequently breaks down. Significantly, in this form of the invention, the tissue adhesive can also act as a healing promoter for the tissue. In this form of the invention, the tissue adhesive is preferably in the form of a gel.

And in another particularly preferred application, a tissue adhesive, comprising a mixture of natural polymers and an aqueous solution of a water soluble starch or a water soluble starch derivative which forms a gel with the addition of the mixture of natural polymers, is positioned at a burn site, or a skin donor site, or a skin graft site, etc., with the tissue adhesive adhering to the burn site, or the skin donor site, or the skin graft site, etc. and acting as a healing promoter and as a protective cover for the burn site, or the skin donor site, or the skin graft site, etc. until the tissue adhesive subsequently breaks down. In this form of the invention, the tissue adhesive may be in the form of a gel or a thin film device.

EXAMPLES

In all of the examples which follow, the chitosan used was high molecular weight chitosan obtained from Sigma-Aldrich, and the sodium alginate used was obtained from willpowder.com. White vinegar was used as the acetic acid source. The white vinegar and other materials were obtained locally.

Examples 1-6—Shear Testing for Adhesive Strength

The shear tests (see K. Vakalopoulos et al., "*Mechanical Strength and Rheological Properties of Tissue Adhesives With Regard to Colorectal Anastomosis*", Annals of Surgery, Volume 261, Number 2, February 2015, pp 323-331) were performed on specimens of thin sliced (⅛") beef round bottom that were 3 centimeters by 4 centimeters in size to provide 12 square centimeters for the adhesion surface. These specimens were washed with water and blotted dry with a paper towel. Each surface was then irrigated with the activating agent solution (~1 ml per surface) and then 0.30 grams of the adhesive powder to be tested was sprinkled uniformly on each surface. The two adhesion test surfaces were again irrigated with the activating agent and the two surfaces joined. The specimen was pressed with 2 pounds of weight for 5 seconds before being placed in the shear test rig such that one surface was held stationary and the other was supporting the added weight. Weight was then added incrementally until separation of the specimen occurred. Results are shown in Table I.

TABLE I

| Sample ID | Adhesive Used | Activating Agent | Separation Weight Grams |
|---|---|---|---|
| Comparative A | 75:25 Sodium Alginate:Chitosan | Normal Saline | 96.6 |
| Comparative B | Sodium Alginate | 4% Acetic Acid | 163.0 |
| Comparative C | Chitosan | 4% Acetic Acid | 128.0 |
| Example 1 | 75:25 Sodium Alginate:Chitosan | 4% Acetic Acid | 274.5 |
| Example 2 | 50:50 Sodium Alginate:Chitosan | 4% Acetic Acid | 225.0 |
| Example 3 | 25:75 Sodium Alginate:Chitosan | 4% Acetic Acid | 116.7 |
| Example 4 | 75:25 Sodium Alginate:Chitosan | 4% Lactic Acid | 193.7 |

Comparative Example A versus Example 1 shows that the dilute acetic acid activator provides significantly enhanced adhesion versus normal saline. Comparative Examples B and C versus Examples 1, 2 and 4 show enhanced adhesion for the mixture of the two natural polymers over the adhesion observed for the individual polymers. Example 1 demonstrates an adhesion of 22.9 grams/square centimeter.

The procedure as described above was followed with the addition of 0.10 gram of a therapeutic agent to the 75:25 sodium alginate:chitosan powder. In Example 5, acetaminophen was used as the therapeutic agent, and in Example 6 the therapeutic agent was naproxen. As can be seen in Table II, there was a small decrease in adhesive strength versus Example 1 with the therapeutic added, but the adhesive strength was still greater than all Examples other than Example 1. Results are summarized in Table II.

TABLE II

| Sample ID | Therapeutic Used | Adhesion Decrease | Separation Weight Grams |
|---|---|---|---|
| Example 5 | Acetaminophen | 7% | 255.5 |
| Example 6 | Naproxen | 12% | 241.5 |

Table II illustrates that therapeutic agents may be added to the adhesive formulation with only a small decrease in adhesive strength to maintain adhesion within a range appropriate for the applications cited.

Examples 7 And 8—Gel Durability Testing

A gel was formed by adding first 6 ml of the activating agent to a small ceramic cup, followed by 0.35 grams of 75:25 Sodium Alginate:Chitosan. This was thoroughly mixed to form a soft and workable gel. This was used as the Comparative Example D, and to this was added 10 ml of normal saline solution. This was then covered to prevent evaporation and allowed to sit for 48 hours. In Examples 7 and 8, the same procedure was used with the exception that the gel was treated with a 2% by weight aqueous solution of a calcium salt before being exposed to saline. Calcium chloride was used in Example 7, and calcium carbonate in Example 8. After the saline was removed, the gel was weighed and subjected to a pressurized water jet to determine integrity. Water pressure at gel breakup with a normal water stream from a faucet or a Waterpik™-type device was observed. Results are shown in Table III.

TABLE III

| Sample ID | Calcium Salt Used | Activating Agent | Weight Gain | Gel Integrity |
|---|---|---|---|---|
| Comparative D | None | 4% Acetic Acid | 5.2 grams | Soft Gel - No integrity |
| Example 7 | Calcium chloride | 4% Acetic Acid | 4.0 grams | Firm Gel Breakup with water pik at 80 psig |
| Example 8 | Calcium carbonate | 4% Acetic Acid | 6.0 grams | Medium Firm Gel Integrity lost with normal faucet stream |

Comparative Example D versus Examples 7 and 8 show that the resistance of the gel to body fluid is improved with the calcium treatment for retention of the integrity of the gel. Fluid absorption is decreased with the calcium chloride treatment.

Examples 9 and 10—Use of a Water Soluble Starch Derivative to Form A Gel with Adhesive and Wound Healing Properties Example 9 (Without Activating Agent): A gel was formed by adding 0.15 grams of 75:25 sodium alginate:chitosan powder to 3 ml of a 2.4 weight percent aqueous solution of pullulan (a fermented starch derivative). On mixing, this formed a clear uniform gel. This gel was applied in a thin layer to a specimen of beef bottom round and the gel was sprayed with a 2% calcium chloride solution toughening agent. The resulting film was resistant to a Waterpik™ spray of body temperature water and only showed erosion with the spray four inches from the specimen.

Example 10 (With Activating Agent): A gel was formed by adding 0.15 grams of 75:25 sodium alginate:chitosan powder to 3 ml of a 2.4 weight percent aqueous solution of pullulan (a fermented starch derivative). On mixing, this formed a clear uniform gel. To this was added 0.25 ml of white vinegar (the activating agent) followed by thorough mixing. The resulting clear, sticky gel was applied in a thin layer to a specimen of beef bottom round and the gel was sprayed with a 2% calcium chloride solution toughening agent. The resulting film was resistant to a Waterpik™ spray of body temperature water and only showed erosion with the spray one inch from the specimen.

Examples 11-15—Preparation of a Thin Film Device with and without A Water Soluble Starch Derivative Example 11 (Gel Stability Testing where the Gel Uses a Water Soluble Starch Derivative): A gel was formed by adding 0.15 grams of 75:25 sodium alginate:chitosan powder to 3 ml of a 2.4 weight percent aqueous solution of pullulan (a fermented starch derivative). On mixing, this formed a clear uniform gel. To this was added 0.5 ml of white vinegar (the activating agent) followed by thorough mixing. The resulting clear, sticky gel was applied in a thin layer onto waxed paper and this was applied to a two inch square of paper towel which had been wet with a 2% calcium chloride solution (the toughening agent). The waxed paper was peeled away and the film on the paper towel was applied to a specimen of beef bottom round. The film was then sprayed again with 2% calcium chloride solution toughening agent. The resulting film was resistant to a Waterpik™ spray of body temperature water and only showed erosion with the spray two inches from the specimen.

Example 12 (Gel Stability Testing where the Gel does not Use A Water Soluble Starch Derivative): A Gel was Formed by Adding First 6 ml of white vinegar activating agent to a small ceramic cup, followed by 0.35 grams of 75:25 Sodium Alginate:Chitosan. This was thoroughly mixed to form a soft and workable gel. The gel was immediately applied to a beef round bottom sample as a film, and the film was then sprayed with a 2% calcium chloride solution as a toughening agent. The resulting gel was resistant to a body temperature Waterpik™ spray to 7 inches.

Example 13 (Gel Stability Testing Where The Gel Does Not Use A Water Soluble Starch Derivative): A gel was formed by adding first 6 ml of white vinegar activating agent to a small ceramic cup, followed by 0.35 grams of 75:25 Sodium Alginate:Chitosan. This was thoroughly mixed to form a soft and workable gel. The gel was placed in a 10 cc syringe and all air removed from the syringe. After two hours at room temperature, the gel from the syringe was applied to a beef round bottom sample as a film, and the film was then sprayed with a 2% calcium chloride solution as a toughening agent. The resulting gel was resistant to a body temperature Waterpik™ spray to 17 inches.

Examples 12 and 13 demonstrate that the gel prepared without the soluble starch derivative is an effective adhesive if applied immediately, but does not maintain adhesive qualities over a short period of time.

Example 14 (Gel Stability Testing Where The Gel Uses A Water Soluble Starch Derivative): A gel was formed by adding first 3 ml of 2.4 wt. % pullulan solution to a small ceramic cup, followed by 0.15 grams of 75:25 Sodium Alginate:Chitosan. This was thoroughly mixed to form a soft and workable gel. To this was added 0.25 ml of white vinegar, followed by further mixing. The gel was immediately applied to a beef round bottom sample as a film, and the film was then sprayed with a 2% calcium chloride solution as a toughening agent. The resulting gel was resistant to a body temperature Waterpik™ spray to 5 inches.

Example 15 (Gel Stability Testing Where The Gel Uses A Water Soluble Starch Derivative): A gel was formed by adding first 3 ml of 2.4 wt. % pullulan solution to a small ceramic cup, followed by 0.15 grams of 75:25 Sodium Alginate:Chitosan. This was thoroughly mixed to form a soft and workable gel. To this was added 0.25 ml of white vinegar (the activating agent), followed by further mixing. The gel was placed in a small capped vial for 28 days. No separation of components or settling of solids was observed over this time. The gel was applied to a beef round bottom sample as a film, and the film was then sprayed with a 2% calcium chloride solution as a toughening agent. The resulting gel was resistant to a body temperature Waterpik™ spray to 5 inches.

Examples 14 and 15 demonstrate that the gel prepared with the soluble starch derivative is an effective adhesive if applied immediately and maintains adhesive qualities over at least a 28 day period.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A tissue adhesive gel for application to a tissue site, the tissue adhesive gel consisting of:
   a mixture of an alginate and chitosan, wherein the ratio of alginate to chitosan is between 10:90 and 90:10; and
   a 2-5% by weight aqueous solution of pullulan.

2. The tissue adhesive gel according to claim 1 wherein the tissue site comprises at least one from the group consisting of a surgical site created during tonsillectomy surgery, a surgical site created during adenoidal surgery, a burn site, a skin donor site, a skin graft site and a joinder site between two pieces of tissue.

3. The tissue adhesive gel according to claim 1 wherein the alginate is sodium alginate.

4. The tissue adhesive gel according to claim 3 wherein the ratio of sodium alginate to chitosan is between 25:75 and 75:25.

5. The tissue adhesive gel according to claim 1 wherein the gel is dried so as to form a film.

6. The tissue adhesive gel according to claim 1 wherein the tissue adhesive breaks down at least 2 days after application to a tissue site.

7. A tissue adhesive gel for application to a tissue site, the tissue adhesive gel consisting of:
   a mixture of an alginate and chitosan, wherein the ratio of alginate to chitosan is between 10:90 and 90:10;
   an aqueous solution of acetic acid, wherein the weight percent of the acetic acid solution is between 0.001-3%; and
   a 2-5% by weight aqueous solution of pullulan.

8. The tissue adhesive gel according to claim 7 wherein the alginate is sodium alginate.

9. The tissue adhesive gel according to claim 8 wherein the ratio of sodium alginate to chitosan is between 25:75 and 75:25.

10. The tissue adhesive gel according to claim 7 wherein the tissue site comprises at least one from the group consisting of a surgical site created during tonsillectomy surgery, a surgical site created during adenoidal surgery, a burn site, a skin donor site, a skin graft site and a joinder site between two pieces of tissue.

11. A tissue adhesive for application to a tissue site, the tissue adhesive comprising:
   a first adhesive surface for application to the tissue site, wherein the first adhesive surface comprises:
      a mixture of sodium alginate and chitosan, wherein the ratio of sodium alginate to chitosan is between 10:90 and 90:10; and
      a 2-5% by weight aqueous solution of pullulan; and
   a second toughened surface opposite to the first surface, wherein the second toughened surface comprises calcium alginate.

12. The tissue adhesive according to claim 11 further comprising at least one additional therapeutic agent.

13. The tissue adhesive according to claim 12 wherein the at least one additional therapeutic agent is selected from the group consisting of an analgesic compound, an anesthetic compound, a vasoconstrictive compound and an anti-infective compound.

14. The tissue adhesive according to claim 12 wherein the at least one additional therapeutic agent comprises acetaminophen.

15. The tissue adhesive according to claim 12 wherein the at least one additional therapeutic agent comprises naproxen.

16. The tissue adhesive according to claim 11 further comprising an activating agent.

17. The tissue adhesive according to claim 16 wherein the activating agent is a dilute aqueous solution of an acid.

18. The tissue adhesive according to claim 17 wherein the acid is a carboxylic acid.

19. The tissue adhesive according to claim 18 wherein the carboxylic acid is selected from the group consisting of acetic acid and lactic acid.

20. The tissue adhesive according to claim 11 wherein the tissue site comprises at least one from the group consisting of a surgical site created during tonsillectomy surgery, a surgical site created during adenoidal surgery, a burn site, a skin donor site, a skin graft site and a joinder site between two pieces of tissue.

21. The tissue adhesive according to claim 11 wherein the ratio of sodium alginate to chitosan is between 25:75 and 75:25.

* * * * *